United States Patent
Price et al.

(10) Patent No.: US 7,515,059 B2
(45) Date of Patent: *Apr. 7, 2009

(54) PATIENT SUPPORT SURFACE WITH PHYSIOLOGICAL SENSORS

(75) Inventors: James H. Price, Mount Pleasant, SC (US); Geoffrey L. Taylor, Winnipeg (CA); James Milton Cherry Thomas, Mount Pleasant, SC (US); James R. Stolpmann, Bakersville, NC (US); Karl N. Caldwell, Summerville, SC (US); Marla D. Repik, Charleston, SC (US); Nick Bries, Charleston, SC (US); Kerry J. Mensching, Mount Pleasant, SC (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/942,032

(22) Filed: Nov. 19, 2007

(65) Prior Publication Data

US 2008/0060138 A1    Mar. 13, 2008

Related U.S. Application Data

(63) Continuation of application No. 10/827,810, filed on Apr. 20, 2004, now Pat. No. 7,330,127, which is a continuation of application No. 09/673,437, filed as application No. PCT/US99/25311 on Oct. 28, 1999, now Pat. No. 6,721,980.

(60) Provisional application No. 60/105,942, filed on Oct. 28, 1998.

(51) Int. Cl.
*G08B 21/00* (2006.01)

(52) U.S. Cl. ........................... 340/666; 73/172

(58) Field of Classification Search .............. 340/666, 340/665, 667, 575; 200/85 R, 85 A; 73/172; 177/144

See application file for complete search history.

(56) References Cited

U.S. PATENT DOCUMENTS

| | | |
|---|---|---|
| 2,194,809 A | 3/1940 | Powell, Jr. |
| 3,325,799 A | 6/1967 | Farris |
| 3,631,438 A | 12/1971 | Lewin |
| 3,644,950 A | 2/1972 | Lindsay, Jr. |
| 3,727,606 A | 4/1973 | Sielaff |
| 3,836,900 A | 9/1974 | Mansfield |
| 4,146,885 A | 3/1979 | Lawson, Jr. |
| 4,195,287 A * | 3/1980 | McCoy et al. ............. 340/666 |
| 4,245,651 A | 1/1981 | Frost |
| 4,481,686 A | 11/1984 | Lacoste |
| 4,483,029 A | 11/1984 | Paul |
| 4,485,505 A | 12/1984 | Paul |
| 4,525,885 A | 7/1985 | Hunt et al. |
| 4,559,656 A | 12/1985 | Foster |

(Continued)

FOREIGN PATENT DOCUMENTS

JP    06315424 A2    11/1994

*Primary Examiner*—John A Tweel, Jr.
(74) *Attorney, Agent, or Firm*—Barnes & Thornburg LLP

(57) ABSTRACT

A patient support surface comprises a cover defining an interior region, a modifiable support layer situated in the interior region and having at least one air bladder, and a sensor layer situated in the interior region and having at least one sensor configured to detect a physiological parameter of a patient atop the patient support surface.

40 Claims, 10 Drawing Sheets

U.S. PATENT DOCUMENTS

| | | |
|---|---|---|
| 4,564,965 A | 1/1986 | Goodwin |
| 4,595,023 A | 6/1986 | Bonnet |
| 4,602,643 A | 7/1986 | Dietz |
| 4,637,083 A | 1/1987 | Goodwin |
| 4,657,026 A | 4/1987 | Tagg |
| 4,681,098 A | 7/1987 | Lee |
| 4,694,520 A | 9/1987 | Paul et al. |
| 4,757,825 A | 7/1988 | Diamond |
| 4,799,276 A | 1/1989 | Kadish |
| 4,838,309 A | 6/1989 | Goodwin |
| 4,934,468 A | 6/1990 | Koerber, Sr. et al. |
| 4,935,968 A | 6/1990 | Hunt et al. |
| 4,942,635 A | 7/1990 | Hargest et al. |
| 4,949,412 A | 8/1990 | Goode |
| 4,949,414 A | 8/1990 | Thomas et al. |
| 4,971,065 A | 11/1990 | Pearce |
| 5,010,772 A | 4/1991 | Bourland et al. |
| 5,052,067 A | 10/1991 | Thomas et al. |
| 5,057,819 A | 10/1991 | Valenti |
| 5,060,174 A | 10/1991 | Gross |
| 5,117,518 A | 6/1992 | Schild |
| 5,170,364 A | 12/1992 | Gross et al. |
| 5,182,826 A | 2/1993 | Thomas et al. |
| 5,184,112 A | 2/1993 | Gusakov |
| 5,283,735 A | 2/1994 | Gross et al. |
| 5,539,942 A | 7/1996 | Melou |
| 5,664,270 A | 9/1997 | Bell et al. |
| 5,794,288 A | 8/1998 | Soltani et al. |
| 5,815,864 A | 10/1998 | Sloop |
| 5,817,146 A * | 10/1998 | Augustine .................... 607/104 |
| 5,829,081 A | 11/1998 | Pearce |
| 5,873,137 A | 2/1999 | Yavets-Chen |
| 5,934,280 A | 8/1999 | Viard et al. |
| 5,964,720 A | 10/1999 | Pelz |
| 5,970,789 A | 10/1999 | Meyer et al. |
| 6,009,580 A | 1/2000 | Caminade et al. |
| 6,011,477 A * | 1/2000 | Teodorescu et al. ......... 340/575 |
| 6,034,526 A | 3/2000 | Montant et al. |
| 6,079,068 A | 6/2000 | Viard |
| 6,094,762 A | 8/2000 | Viard et al. |
| 6,212,718 B1 | 4/2001 | Stolpmann et al. |
| 6,493,568 B1 | 12/2002 | Bell et al. |
| 6,721,980 B1 | 4/2004 | Price et al. |
| 6,739,006 B2 * | 5/2004 | Borders et al. |
| 7,245,956 B2 | 7/2007 | Matthews et al. |
| 7,330,127 B2 * | 2/2008 | Price et al. .................... 340/666 |
| 2005/0190062 A1 | 9/2005 | Sullivan et al. |
| 2005/0190068 A1 | 9/2005 | Gentry et al. |

* cited by examiner

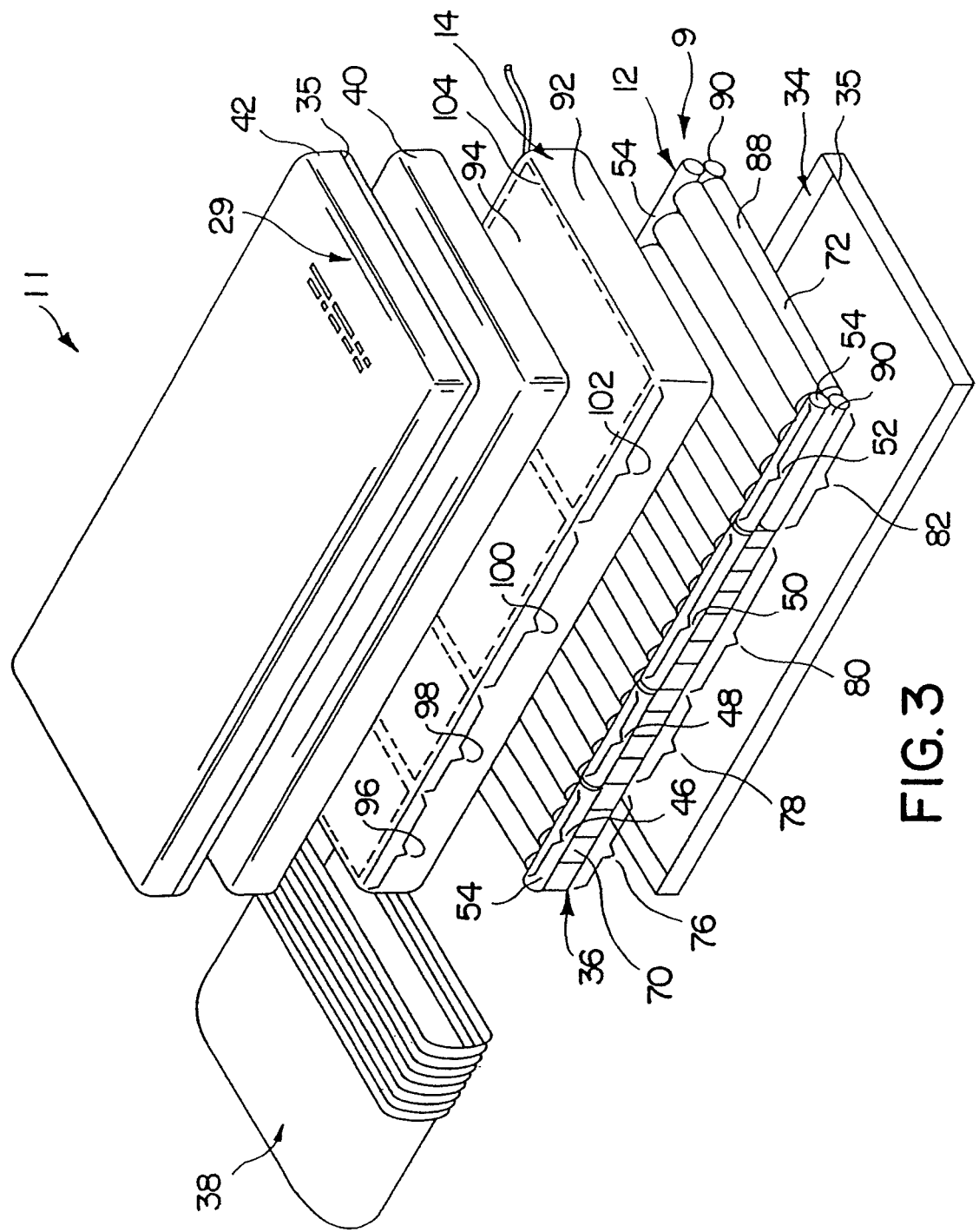

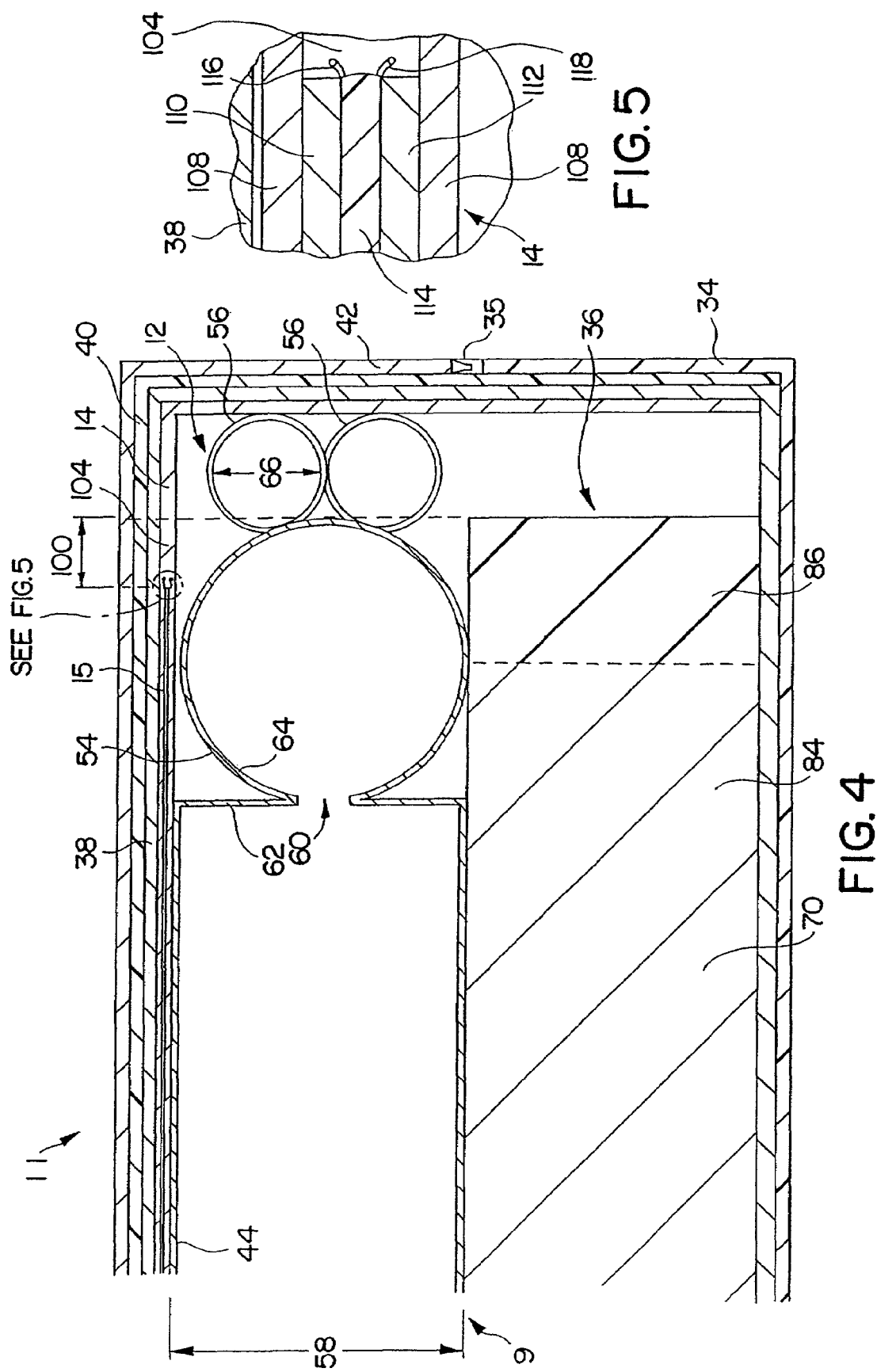

7,515,059 B2

PATIENT SUPPORT SURFACE WITH PHYSIOLOGICAL SENSORS

CROSS REFERENCE TO RELATED APPLICATIONS

This application is a continuation of U.S. patent application Ser. No. 10/827,810, filed Apr. 20, 2004, now U.S. Pat. No. 7,330,127, which, in turn, is a continuation of U.S. patent application Ser. No. 09/673,437, filed Oct. 16, 2000, now U.S. Pat. No. 6,721,980, which is a national phase of PCT/US99/25311, having an International filing date of Oct. 28, 1999, which claims the benefit of U.S. Prov. Pat. App. Ser. No. 60/105,942, filed on Oct. 28, 1998, all of which are hereby expressly incorporated by reference herein.

BACKGROUND AND SUMMARY OF THE INVENTION

The present disclosure relates to controllable surfaces, and particularly to surfaces for preventing and treating pressure ulcers.

Pressure ulcers in bedridden patients can be caused by excessive forces between the patient and a surface upon which the patient is resting. It is known to provide controllable mattresses that allow for adjusting pressures within a mattress surface. For example, it is known to adjust air pressure within multiple chambers of an air mattress, to reduce interface forces over a given bony protuberance based on sensed air pressures within the chambers.

According to the present disclosure, an interface sensing system eliminates the need to conduct independent interface force testing for a patient at each body and bed position on an ongoing basis. An intelligent control system is provided for adjusting internal cushion pressures in a mattress surface based on interface force measurements.

In the present disclosure, a method of minimizing a force between a modifiable support surface and a patient located thereon includes the steps of establishing an initial recorded force between the patient and the support surface, performing a first procedure including modifying the support surface in a first manner for a predetermined time increment, measuring the current force between the patient and the surface, comparing the current force to the recorded force, and replacing the recorded force with the current force. The first procedure is repeated so long as the current force is less than the recorded force, then a second procedure is performed including modifying the support surface in a second manner for a predetermined time increment, measuring the current force between the patient and the support surface, comparing the current force to the recorded force, and replacing the recorded force with the current force. The second procedure is repeated so long as the current force is less than the recorded force.

In the present disclosure, a support surface apparatus includes at least one support member for supporting a person, and a force sensor located on the at least one support member. The force sensor is configured to measure a force between the person and the at least one support member. The apparatus also includes a mechanism configured to adjust a support characteristic of the at least one support member based upon the force detected by the force sensor to minimize the force between the person and the at least one support member.

In an illustrated embodiment of the present disclosure, a support surface apparatus includes at least one air bladder for supporting a person, a force sensor located on the at least one air bladder, an air supply coupled to the at least one air bladder, and a controller coupled to the force sensor. The force sensor is configured to measure a force between the person and the at least one air bladder. The controller is configured to adjust air pressure within the at least one air bladder based on the force detected by the force sensor to minimize the force between the person and the at least one bladder.

In addition, sensors contained within the force optimization surface of the present disclosure eliminate the need for individual equipment and monitors for measuring specific patient parameters such as heart rate, temperature, and respirations. An apnea monitor is provided to reduce and/or prevent occurrences of episodes of apnea. A built-in weight sensor system eliminates the need for external, cumbersome scales.

Additional features, which alone or in combination with any other feature(s), such as those listed above and those listed in the appended claims, may comprise patentable subject matter and will become apparent to those skilled in the art upon consideration of the following detailed description of illustrative embodiments exemplifying the best mode of carrying out the embodiments as presently perceived.

BRIEF DESCRIPTION OF THE DRAWINGS

The detailed description particularly refers to the accompanying figures in which:

FIG. 3 is an exploded view of the support surface system of FIG. 1 showing a bottom cover, foam support layer, air support layer, sensor layer, fire barrier, anti-sheer layer, and top cover;

FIG. 4 is a sectional view along line 4-4 of the support surface of FIG. 1;

FIG. 5 is a blowup of the cross section of the sensor layer enclosed in circle 5 in FIG. 4;

DETAILED DESCRIPTION OF THE DRAWINGS

Figure 1:
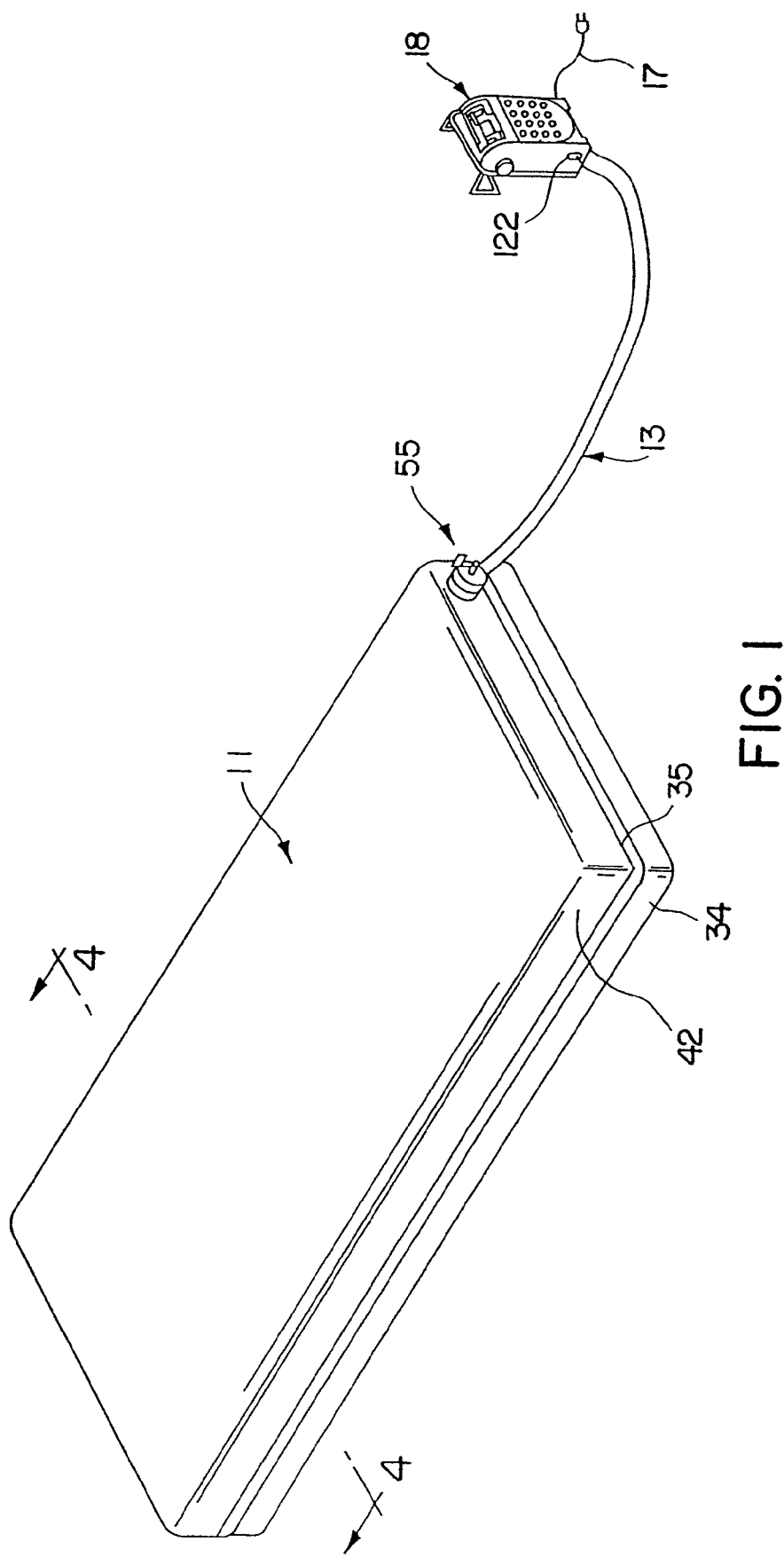
FIG. 1 is a perspective view of a support surface system, lead/tubing assembly and control interface assembly according to the present disclosure.

Referring to FIG. 1, a force optimization surface 10 includes a support surface assembly 11, a control interface assembly or controller 18, and a lead/tubing assembly 13. Support surface assembly 11 includes a bottom cover 34, a modifiable support surface or modifiable support layer 9, a sensor layer 14, a fire barrier 38, an anti-sheer layer 40, and a top cover 42 as shown, for example in FIGS. 3 and 4. In the illustrated embodiment modifiable support layer 9 includes a lower or foam/air support layer 36 and an upper or controllable air mattress layer 12. Air mattress 12 includes one or more independently controllable air zones or chambers. An alternative support surface assembly 11 which can be modified by the addition of sensor layer 14 and fire barrier 38 as described herein for use as support surface assembly 11 in accordance with the present disclosure is described in U.S. Pat. No. 6,212,718, the disclosure of which is incorporated herein by this reference. While the illustrated embodiment increases and decreases pressure in air mattress 12 to modify modifiable support layer 9 in two different manners, it is within the teaching of the disclosure to provide mechanically or electrically modifiable support layers 9 made of foam, springs, or other suitable material which modify the firmness or surface configuration of the support layer in different manners to affect the force between the support surface 11 and a patient 16.

In the illustrated embodiment, air mattress 12 includes individual cylindrical cushions 44 divided into four independently controllable zones or groups referred to as head chamber 46, upper torso chamber 48, lower torso chamber 50 and foot chamber 52, two headers or plenums 54 per chamber, and four side bladders 56 per chamber (not shown in FIG. 3, only two of which are shown in FIG. 4). Each cushion 44 and plenum 54 is illustratively 4.0 inches (10.16 cm) in diameter 58. Each plenum 54 is fluidly coupled to each cylindrical cushion 44 in its associated chamber such as by opening 60 formed through end wall 62 of cylinder 44 and sidewall 64 of plenum 54 as shown, for example, in FIG. 4. Each plenum 54 is also coupled to an air supply 23 including a pump 31 and a blower 33 in controller 18 via mattress plumbing (not shown) coupled to lead/tubing assembly 13. Appropriate mattress plumbing is known and a specific embodiment applicable to the present disclosure is disclosed in U.S. Pat. No. 6,212,718. Each side bladder 56 is 1.5 inches (3.81 cm) in diameter 66. Illustratively each cushion 44, plenum 54, and side bladder 56 is fabricated from urethane coated nylon twill material radio frequency welded to join and seal the fabric in the illustrated geometry.

Illustratively head chamber 46 includes four individual cushions 44 and upper torso chamber 48 includes four individual cushions 44 so that each chamber 46, 48 has an overall length of sixteen inches (40.64 cm). Lower torso chamber 50 includes seven individual cushions 44 and thus has an overall length of twenty-eight inches (71.12 cm). Foot chamber 52 includes five individual cushions 44 and thus has an overall length of twenty inches (50.8 cm).

The manner of inflation of side bladders 56 is not illustrated but may be accomplished through manual inflation valves (not shown) or by having side bladders 56 in fluid communication with one of the chambers 46, 48, 50, 52. Side bladders 56 allow the width of mattress 12 to be adjusted to accommodate common intensive care unit ("ICU") and medical-surgical ("med-Surg") frames. Typical ICU and Med-Surg frames include patient support surfaces having a width of 32-35 inches (81.28-88.9 cm). Illustratively air mattress 12 has a length of approximately 80 inches (203.2 cm) and a width adjustable between thirty-two inches (81.28 cm) (with side bladders deflated) and thirty-five inches (88.9 cm) (with side bladders inflated).

As shown in FIG. 3, bottom layer 36 includes a plurality of foam segments 70 and air support segment 72. As with air mattress layer 12, bottom layer 36 is divided into four segments, a head zone 76, an upper torso zone 78, a lower torso zone 80, and a foot zone 82. Illustratively head zone 76, upper torso zone 78, and lower torso zone 80 each include a plurality of urethane foam segments 70 inserted into urethane coated nylon twill sleeves. The sleeves are joined at regular intervals. This joining may be accomplished in the manner disclosed in U.S. Pat. No. 6,212,718. Foot zone 82 includes air support segment 72 having a plurality of air bladders 88 and plenums 90 underlying foot chamber 52 of air mattress 12.

Each foam segment 70 of head, upper torso, and lower torso zones 76, 78, 80 is thirty-two inches (81.28 cm) in overall length and includes a mid-section 84 extending between two end caps 86. Each foam segment 70 is four inches (10.16 cm) wide by four inches (10.16 cm) tall. Head and upper torso zone 76, 78 illustratively include four foam segments 70 each and thus each zone 76, 78 has an overall length of sixteen inches (40.64 cm). The mid-sections 84 of the foam segments 70 in the head and upper torso zones 76, 78 are a High Resiliency ("HR") grade foam of 2.25-2.5 density, support factor 2.4 minimum, 17-21 ILD, CAL 117, antimicrobial foam. Lower torso zone 80 illustratively includes seven foam segments 70 and thus has an overall length of twenty-eight inches (71.12 cm). The mid-sections 84 of the foam segments 70 in the lower torso zone 80 are a HR grade foam of 2.25-2.5 density, support factor 2.5 minimum, 31-34 ILD, CAL 117, antimicrobial foam.

End caps 86 of all of foam segments 70 of zones 76, 78, 80 combine to form side rails on lower support 36 and are thus referred to as side rail foam. These side rails facilitate patient ingress to and egress from surface 10. In addition, end caps 86 and mid-sections 84 combine to create a cradle zone to facilitate adequate centering of patient to assist in keeping patient from sliding into the side rail and reducing the need for the caregivers to frequently reposition the patient. End caps 86 are bonded to mid-sections 70 with acetone heptane and resin base spray adhesive. Each end cap 86 is two inches (5.08 cm.) in overall length, four inches (10.16 cm) wide, and four inches (10.16 cm) tall to conform to the mid-section 70 to which it is attached. End caps 86 are made of conventional foam grade such as Foam Grade H45XF, 1.8-1.9 PCF, 53-60 ILD, support factor 2.0, Cal 117, antimicrobial foam.

Illustratively foot zone 82 includes air support segment 72 having five air bladders 88 extending between and fluidly coupled to two spaced apart plenums 90. Bladders 88 and plenums 90 are four inches (10.16 cm) in diameter. Thus foot zone 82 has an overall length of twenty inches (50.8 cm). Bladders 88 and plenums 90 are made of urethane coated nylon twill material, IAW material specification 100-001-0032. Bladders and plenums 90 are in fluid communication with the two plenums 54 that supply air to the foot chamber 52 of air mattress 12.

Force optimization surface 10 provides for sensing multiple interface pressures or forces exerted by the modifiable support surface 9 on a patient 16 atop sensor layer 14. Those skilled in the art will recognize that interface pressure measured in a defined area is the integral over the area of all of the forces exerted normal to the area. Therefore, the term force or interface force will be used to refer to the interface force or interface pressure unless otherwise stated to avoid confusion between pressure in an air bladder and the interface pressure. Support surface 11 is coupled to a controller 18 configured with software for regulating air pressure within each chamber 46, 48, 50, 52 of mattress 12 based on measured interface force values exerted by the chambers 46, 48, 50, 52 on the patient 16. Various interface sensors 15 are known which detect the interface pressure and the interface force. In the illustrated embodiment, zones of the modifiable support surface 9 are modified in response to the maximum force exerted within the zone using resistive force sensors located on each zone. A multiplicity of sensors detecting interface pressure can be used to detect this maximum force exerted within the zone, however in the illustrated embodiment an interface force sensor is described. To avoid confusion, the term interface sensor will be used to refer to both a multiplicity of interface pressure sensors or an interface force sensor.

Force optimization surface 10 with its controller 18 uses multiple interface sensor readings to decide how to modify pressure within a given chamber or chambers within mattress 12 to optimally reduce the interface force. The nature of the optimization can vary as desired, such as controlling air pressures to achieve a minimum average value for all interface sensor signal values, to maintain all interface sensor values below a threshold, or to achieve certain force profiles over various surface areas, etc.

Illustratively sensor layer 14 includes a peripheral downwardly extending sidewall 92 and a surface 94 extending between and combining with sidewall 92 to form a modifiable support surface-receiving cavity much like a fitted sheet, as shown for, example, in FIGS. 3 and 4. Nevertheless, it is within the teaching of this disclosure for sensor layer 14 to include a mat disposed between air mattress 12 and top cover 42. Incorporated within surface 94 is a plurality of sensing zones which in the illustrated embodiment include head zone 96, upper torso zone 98, lower torso zone 100, and foot zone 102. In the illustrated embodiment, each sensing zone includes a peripherally extending non-sensing border 104 having a width 106 of one inch (2.54 cm), an outer covering 108, and an interface sensor 15. Illustratively, interface sensor 15 includes a top conductive layer 110 and a bottom conductive layer 112 separated by a semiconductor material 114, a first wire 116 coupled at one end to top conductive layer 110 and at the other end to controller 18, and a second wire 118 coupled at one end to bottom conductive layer 112 and at the other end to controller 18, as shown for, example, in FIGS. 3, 4 and 5. Illustratively outer covering 108 is 0.002 in (0.051 mm) thick aromatic polyether polyurethane film available from Deerfield Urethane (Route S-10 Box 185, South Deerfield, Mass. 01373) PT9200U or equivalent. Each conductive layer 110, 112 is illustratively Monsanto Flextron.™. nickel coated copper rip stop nylon fabric. Semiconductor material 114 is a piezo-resistive sheet available from Verg, Inc, Winnipeg, Canada. Illustrated interface sensor 15 acts to sense the maximum force exerted anywhere within the zone.

In the illustrated embodiment of sensor layer 14, head zone 96 is sixteen inches (40.64 cm) long and thirty-two inches (81.28 cm) wide and is positioned to lie adjacent to head chamber 46 of air mattress 12. Upper torso zone 98 is sixteen inches (40.64 cm) long and thirty-two inches (81.28 cm) wide and is positioned to lie adjacent to upper torso chamber 48 of air mattress 12. Lower torso zone 100 is twenty-eight inches (71.12 cm) long and thirty-two inches (81.28 cm) wide and is positioned to lie adjacent to lower torso chamber 50 of air mattress 12. Foot zone 102 is twenty inches (50.8 cm) long and thirty-two inches (81.28 cm) wide and is positioned to lie adjacent to foot chamber 52 of air mattress 12.

Alternative integrated interface sensing material in sensor layer 14 can be any material that provides multiple interface sensors 15 such as a resistive or capacitive film providing a grid or matrix of interface sensors. These interface pressure mapping technologies are well known to those of skill in the art, and provide for sensing and mapping interface pressures against the entire body contact area of patient 16. Illustrative interface pressure sensing and mapping devices include capacitive devices such as the X-SENSOR.™. pad available from the X-sensor company in Calgary, Canada or the EMED.™. system from Novel GmbH in Munich, Germany, resistive force sensing devices such as those available from Vista Med in Winnipeg, Canada or Tekscan in Boston, Mass., or other sensor types such as pneumatic pressure sensors, etc. It will be understood that in order to determine the maximum force exerted within a zone, like the illustrated interface sensor does, a multiplicity of capacitive or pneumatic sensors would be required within each specific zone.

It will be understood that in the illustrated embodiment, lower support layer 42, air mattress 12, and sensor layer 14 are all divided into the same number and size of segments, chambers, or zones. Each segment, chamber, or zone corresponds and is associated with the chamber, segment, or zone underlying or overlying it. Thus, hereinafter the terms zones of modifiable support surface or zones of support surface assembly are occasionally used.

Referring again to FIGS. 3 and 4, fire barrier 38 is designed to receive and substantially totally encompass lower foam/air layer 36 and upper air mattress support layer 12. Fire barrier 38 is illustratively formed of stretchable 1×1 rib knit that is constructed of fiberglass and modacrylic fabric or equivalent IAW raw material specification 240-02-0019. Anti-shear lining 40 is formed to have a downwardly opening cavity to receive the fire barrier 38 lower support layer 36 and air mattress layer support 12 assembly in the manner of a fitted sheet. Anti-sheer lining 40 is constructed of a low coefficient of friction nylon, polyester twill, or an equivalent. Anti-sheer lining 40 is installed over the fire barrier 38 and air mattress 12 and under the top cover 42 to reduce sheer force to the patient.

Illustratively, top cover 42 and bottom cover 34 each include one half of a peripherally extending zipper 35. The half of the zipper 35 coupled to top cover 42 is sewn to urethane strips for sealing to the host material of top cover 42. Illustratively the host material of top cover 42 is a polyurethane coated, bi-directional stretch nylon substrate material. The half of the zipper 35 coupled to bottom cover 34 is sewn directly to the host material of bottom cover 34. The host material of bottom cover is illustratively a monomeric vinyl laminate fabric. The zipper starts and ends on the center line of the patient foot end 29. Anti shear lining 40, fire barrier 38, upper and lower support layers 12, 36 are received between top and bottom covers and enclosed therein by joining halves of zipper 35 to form support surface structure 11.

Controller 18 includes a smart board 19, a power supply 21, an air supply 23, a control I/O panel 25, and a pneumatic system 27. The illustrated power supply 21 is one of a 220 volt 50 Hz input, 24 volt DC, 110 volt AC output power supply or a 110 volt 50 Hz input, 24 volt DC, 110 volt AC output power supply coupled to power cord 17. Air supply 23 includes an air pump 31 such as a Thomas 0.35 cfm 24 VDC air pump and a blower 33 such as Amatec centrifugal blower each of which are mounted in controller 18, electrically connected to power supply 21 and fluidly coupled to pneumatic system 27. Blower 33 is a high volume low pressure blower used for rapid inflation of the air mattress 12 to bring the mattress to initial set pressures and to bring all zones of the mattress to maximum pressure during a max inflate mode 134. Pump 31 is a high pressure low volume pump used to increase pressures in chambers of air mattress 12.

Illustratively, control I/O panel 25 includes an alarm silence button 37, an alarm silence LED 39, a max inflate button 41, a max inflate LED 43, a zone 1 LED 45 which blinks when selected, a zone 2 LED 47 which blinks when selected, a zone 3 LED 49 which blinks when selected, a zone 4 LED 51 which blinks when selected, and a call for service LED 53. Illustratively, panel 25 is a membrane keypad adhesively secured to controller 18 and is connected to control electronics (not shown) on smart board 19 through a ribbon cable and PCB connector (not shown). Control panel 25 will provide operator feed back via the use of LEDs 39, 43, 45, 47, 49, 51, 53 including alarms and sensor malfunctions.

To meet CPR requirements, a one step manual emergency dump valve 55 is incorporated in a known manner into support surface assembly 11. The purpose of valve 55 is to dump air in the head, upper torso, and lower torso chambers 46, 48, 50 in fifteen seconds. Once CPR is completed, dump valve 55 is reset.

Figure 2:
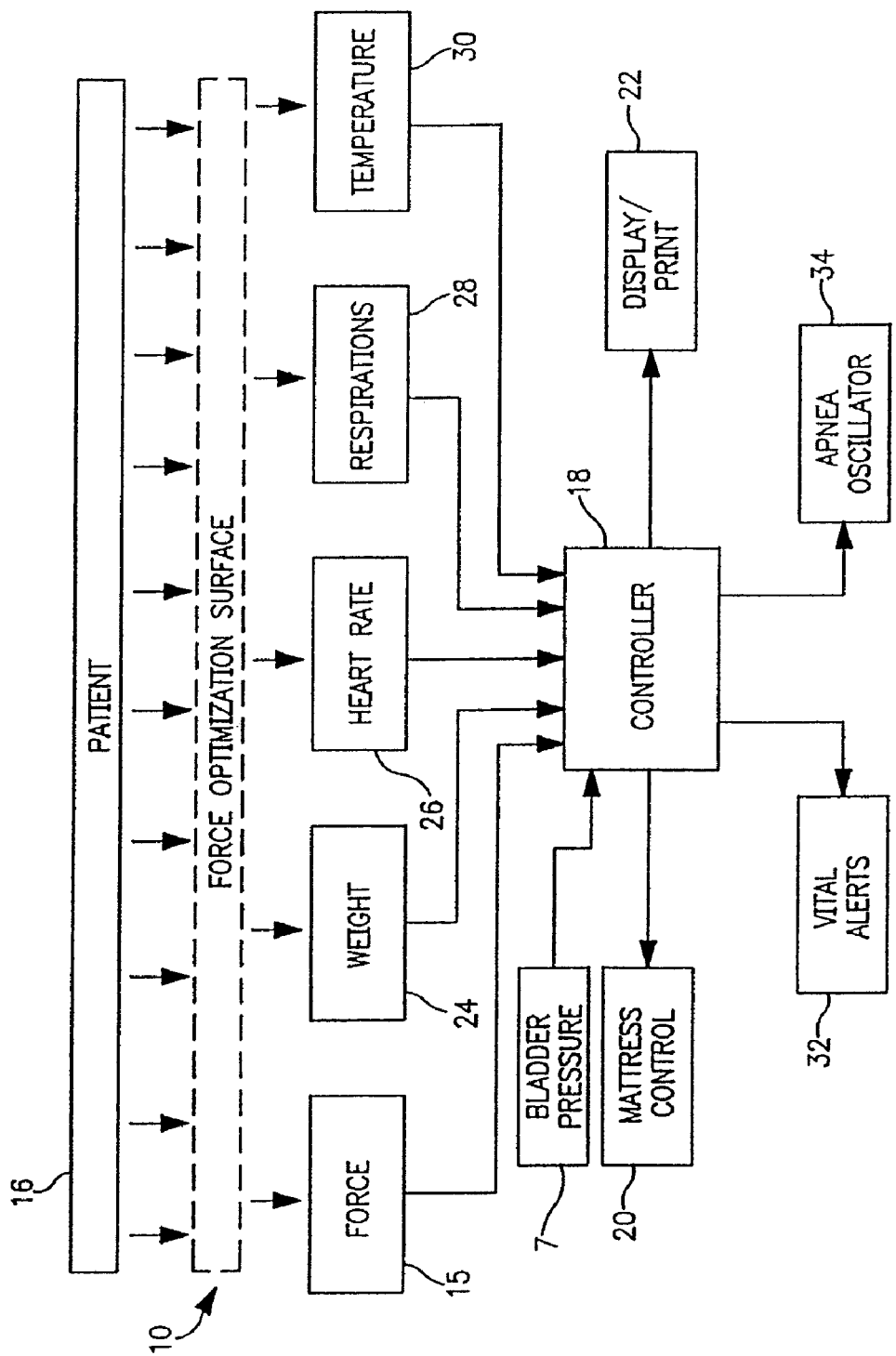
FIG. 2 is a block diagram of a system according to the present disclosure including a controller, force, weight, heart rate, respiration, bladder pressure, and temperature sensors, the controller coupled to mattress control, display/print output, vital alert, and apnea oscillator systems.

Pneumatic system 27 includes four stepper motor controlled zone selector needle valves (not shown), five pressure transducers 7 (shown diagrammatically in FIG. 2 only), a stepper motor controlled vent needle valve (not shown). Pneumatic system 27 is coupled to smart board 19 which includes a processor and firmware (not shown). Pneumatic system 27 includes air supply lines 57 fluidly coupled to each chamber 46, 48, 50, 52. Each supply line 57 is also coupled to the air supply 23 through a designated zone valve (not shown). A pressure sensing line (not shown) is connected to each supply line 57 and to a pressure transducer 7 electrically coupled to smart board 19. A vent line 59 is coupled to each supply line 57 through vent valve (not shown) to vent chambers 46, 48, 50, 52 when appropriate.

Controller 18 provides for measuring sensed interface forces in real time and modifying the modifiable support surface 9, i.e., controlling chamber pressures in air mattress 12 in the illustrated embodiment, as required to reduce interface forces between a patient and support surface assembly 11. Controller 18 is illustratively coupled to a mattress control system 20 that regulates pressure within chambers of mattress 12. For an example of a system that determines an index using pressures for evaluating interface pressure performance of a support surface see U.S. Pat. No. 5,970,789, entitled Method and Apparatus for Evaluating a Support Surface, which is hereby incorporated by reference.

Controller 18 can be provided within force optimization surface 10 or as a separate component coupled to force optimization surface 10 via an appropriate communication interface, such as wires or a wireless communication link. In the illustrated embodiment top and bottom wires 116, 118 from each sensor zone are coupled into an eight wire bundle 120 forming a portion of lead/tubing assembly 13 extending between support surface assembly 11 and terminating in a 9-pin D sub-miniature connector with finger twist lock screws 122 coupled to controller 18. Controller 18 further provides for coupling force optimization surface 10 to other external systems (not shown) over various types of links, such as a peer-to-peer communication network.

Software in controller 18 is configured to scan or monitor interface forces from interface sensors 15 to maintain desired support characteristics, such as minimizing the force between the patient and each zone of support surface assembly 11, regardless of the body position or the bed position. Thus, for example, if patient 16 rolls over onto his or her side, or if support surface assembly 11 is coupled atop an articulated bed frame that assumes a non-flat orientation, controller 18 will adjust pressures in air mattress 12, i.e., modify modifiable support surface 9, automatically to minimize forces between each zone and the patient. These adjustments can be made at a predetermined periodic rate or can be event-driven as required. The rate at which adjustments are made can further be limited or filtered as desired.

The software or firmware loaded into controller 18 includes a start phase 130, a force management phase 132, a max inflate mode 134, and a service mode 136. In describing these phases the term "zone" will be used to refer to the sensing zone 96, 98, 100, 102 and the underlying associated chamber 46, 48, 50, 52 respectively. These zones are referred to as zone 1 (head zone 96 and head chamber 46), zone 2 (upper torso zone 98 and upper torso chamber 48), zone 3 (lower torso zone 100 and lower torso chamber 50) and zone 4 (foot zone 102 and foot chamber 53). "Pressure in a zone" refers to the air pressure in the chamber underlying and associated with the sensing zone. "Force on a zone" refers to the interface force or pressure sensed by interface sensor 15.

Figure 6:
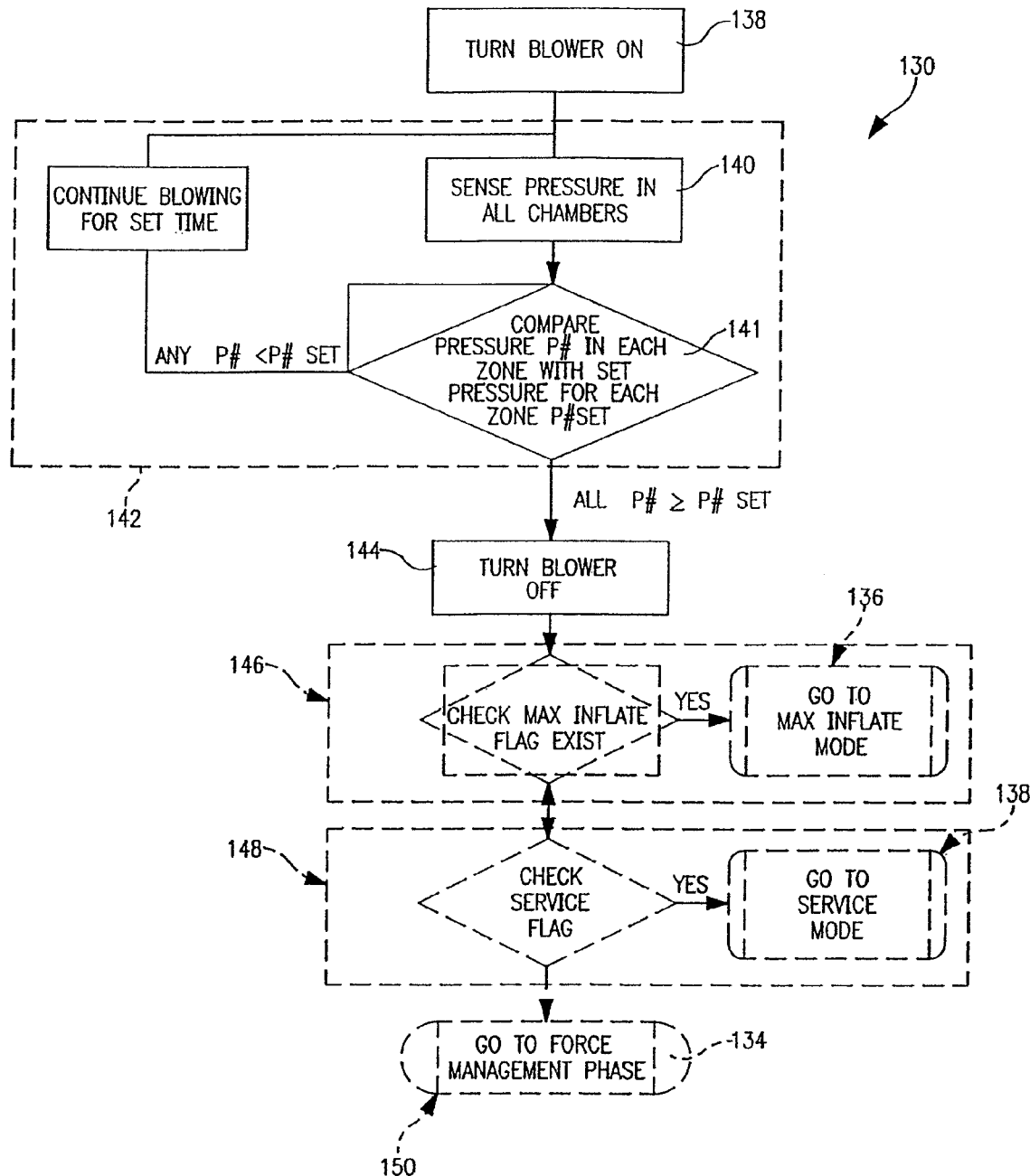
FIG. 6 is a flow diagram of the algorithm for a start phase controlling the inflation of the zones of the air support layer in accordance with the present disclosure.

The algorithm for start phase 130 is shown, for example, in FIG. 6. Start phase 130 includes the steps of turning the blower on 138, sensing the current pressure in zones 1, 2, 3, and 4 ($P_{1-4}$) 140, comparing the current pressure in each zone to a set pressure for each zone 141, blowing air into each zone so long as the pressure in all chambers is not greater than the respective set pressure for the chamber 142, and turning off the blower when the pressure in all zones is greater than a set initial pressure ($P_{set}$) 144. Typically after turning the blower off 144, one or more of the following steps of going to the max inflate mode 136 if the max inflate flag exists 146, going to the service mode 138 if the service flag exists 148, and continuing to the force management phase 132 after completion 150 are included in start phase 130.

Figure 7:
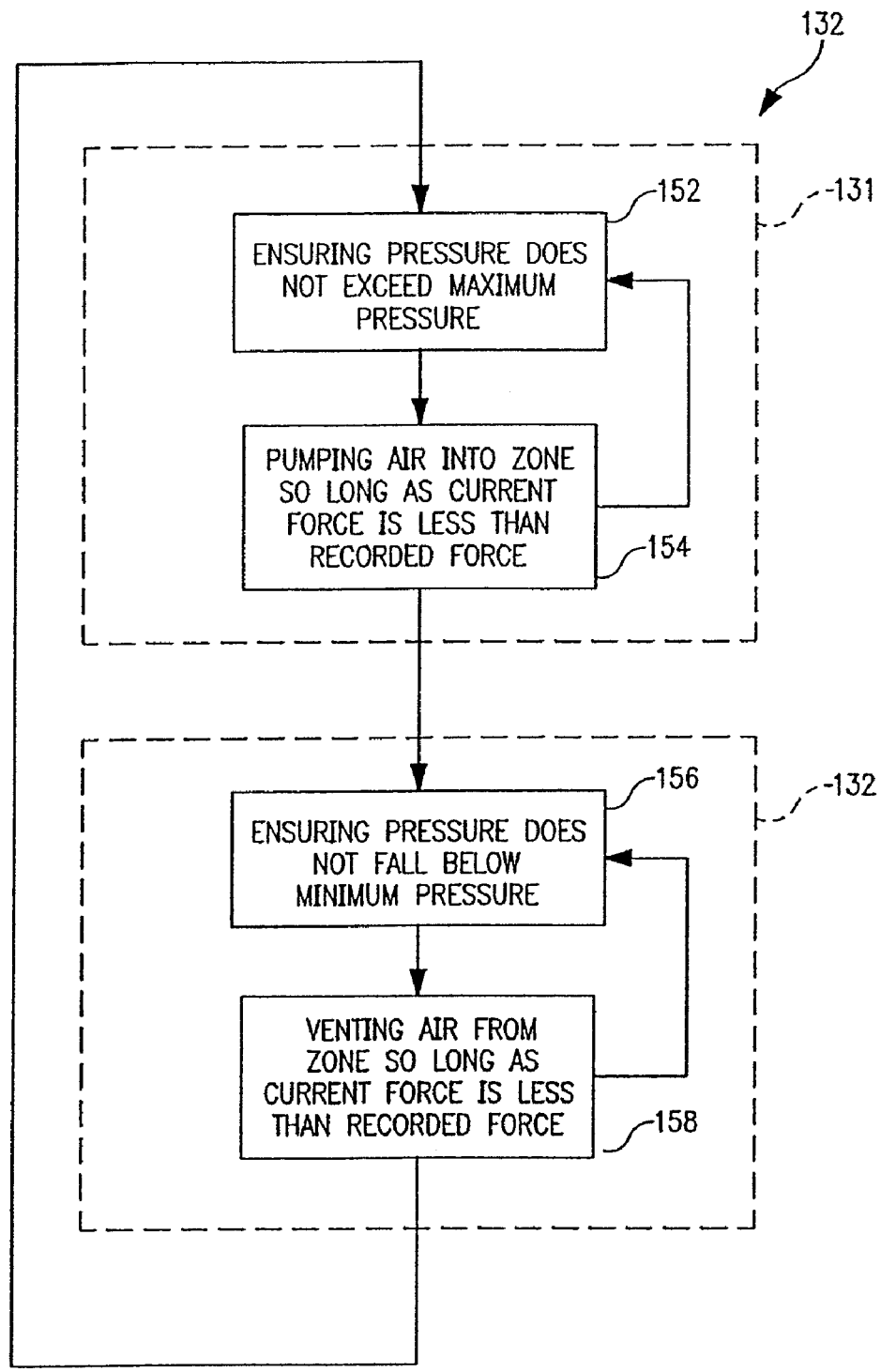
FIG. 7 is a flow diagram of an upper level algorithm for a force management phase for controlling the inflation of the zones of the air support layer in accordance with the present disclosure.

The software includes a force management phase 132 which operates after the start phase 130 to adjust the pressure within each of the chambers underlying the sensor zones to minimize the force exerted between the surface and the patient. As shown, for example, in FIG. 7, at a high level, force management phase 132 includes a first manner of modification of modifiable support surface 9 or pumping procedure 131 and a second manner of modification of modifiable support surface 9 or venting procedure 133. Illustratively, the pumping procedure 131 includes the steps of ensuring that the pressure in a zone ($P_#$) does not exceed a maximum pressure established for the chamber underlying the zone ($P_{\#max}$) before performing any pumping operation 152, and incrementally pumping air into the zone so long as the current force ($F_#$) in the zone is lower than the force recorded prior to the last incremental pumping ($F_{old}$) 154. The venting procedure 133 includes the steps of insuring that the pressure in a zone does not fall below a minimum pressure established for the zone ($P_{\#max}$) before performing any venting operation 156 and incrementally venting the zone when the current force in the zone ($F_#$) exceeds the force recorded prior to the last pumping step ($F_{old}$) 158. The venting procedure 133 is continued so long as the current force ($F_#$) in the zone is less than the force recorded prior to last incremental venting ($F_{old}$), and the venting procedure 133 ceases when the current force in the zone ($F_#$) exceeds the force recorded prior to the last venting step ($F_{old}$). When pumping procedure 131 terminates the force management phase 132 goes to venting procedure 133 and when the venting procedure 133 terminates force management phase 132 returns to pumping procedure 131.

It will be understood that with a plurality of zones overlying a plurality of associated independently inflatable chambers that each zone and its associated chamber could be simultaneously controlled with a dedicated pump, valves and controller or with a single controller, valve manifold, pump, and control algorithm which cycles through the zones. It will also be understood that if modifiable support surface 9 is not an inflatable surface but an otherwise modifiable surface, similar subroutines will be included in pumping and venting procedure 131, 133 to ensure that limits of the modifiable surface are not exceeded and to modify the surface in different manners to facilitate reduction in forces between the surface and the patient. At a very high level force management phase 132 performs a first modification to the support surface so long as it continues to reduce the force between the surface and the patient and then performs a second modification to the surface for so long as it continues to reduce the force between the surface and the patient. Typically after performing the second modification, force management phase returns to the first modification, however if the modifiable support surface 9 can be modified in more than two manners, a third or more modifications may be performed.

Figure 8:
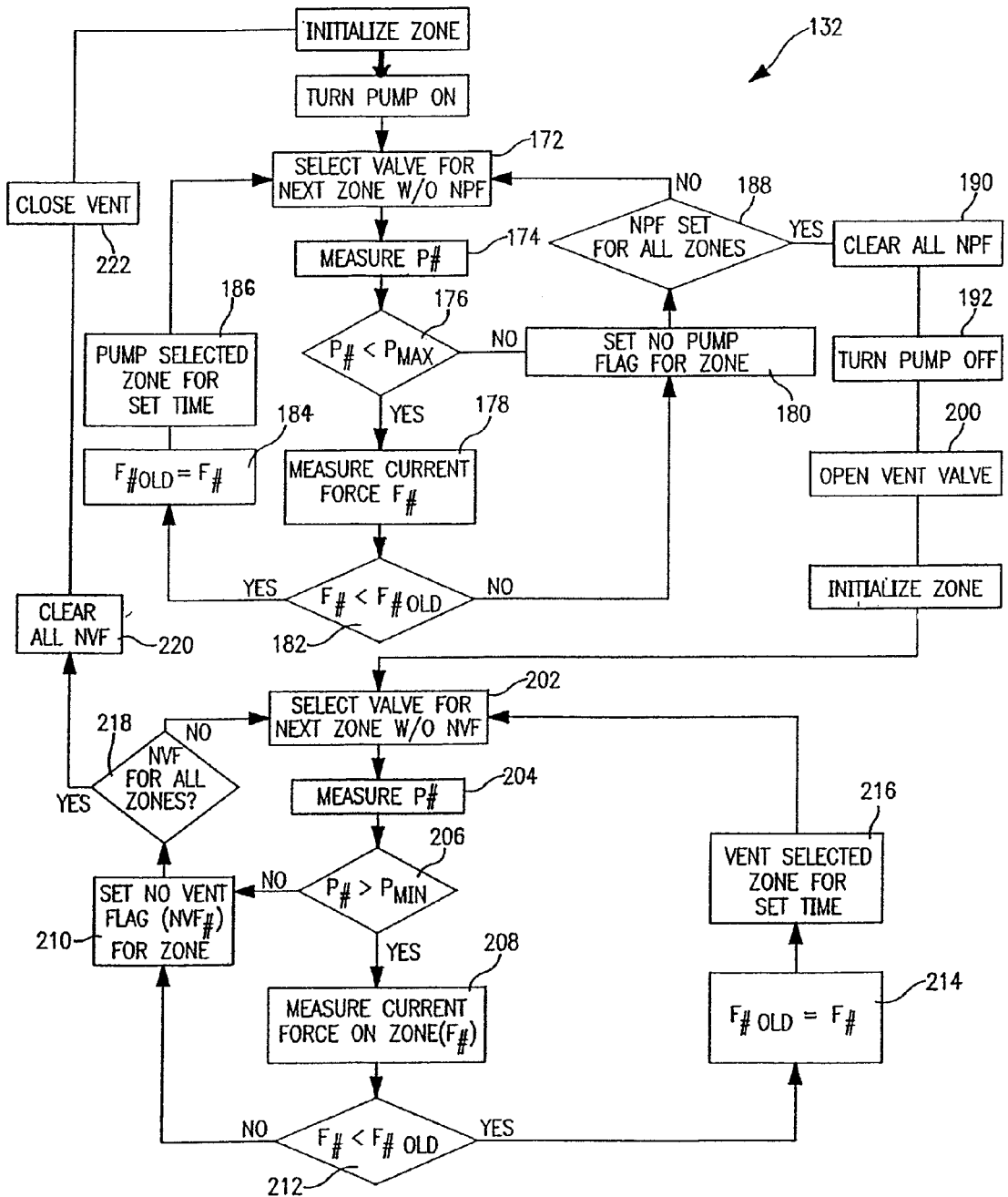
FIG. 8 is a flow diagram of a lower level algorithm for a force management phase for controlling the inflation of the zones of the air support layer in accordance with the present disclosure.

One algorithm for implementing force management phase 132 for multiple zones and a single vent valve and pump is shown in FIG. 8 and includes the pumping procedure 131 and venting procedure 133. Pumping procedure 131 includes the steps of turning on the pump 170, selecting the valve to the next zone which is not in a no pump mode 172, measuring the current pressure ($P_\#$) in the selected zone 174, comparing the current pressure ($P_\#$) in the selected zone to a predetermined max pressure for that zone ($P_{\#max}$) 176. If the current pressure is less than the max pressure ($P_\# < P_{\#max}$) for the zone the step of reading the current force ($F_\#$) on the zone 178 is performed, however, if the current pressure is greater than the maximum pressure then the step of putting the zone into no pump mode by setting the no pump flag for the zone 180 is performed as part of a loop described later either returning to the zone selection step 172 of pumping procedure 131 or exiting to venting procedure 133.

As long as the current pressure does not exceed the maximum pressure for the zone, the step of comparing the current force to the last recorded force on the zone 182 is performed. If the current force on the zone is less than the last recorded force, the goal of minimizing forces is being achieved by what is currently being performed, i.e., pumping, so the steps of replacing the recorded force with the current force ($F_{\#old} = F_\#$) 184 and pumping the zone for a set period of time 186 are performed during a loop that returns to the select zone step 172 of pumping procedure 131.

If during the comparison step 182 it is determined that the current force is not lower than the previously recorded force ($F_\# \geq F_{\#old}$), then whatever is currently being performed, i.e., pumping, is not working to achieve the desired results for the selected zone. Therefore the zone is not pumped anymore and the step of setting a No Pump Flag ($NPF_\#$) to establish that the zone is in a "no-pump mode" 180 is performed as part of a possible pumping procedure exit loop. Anytime the No pump mode step 180 is performed for a zone, that zone cannot be selected anymore during the current pumping procedure as the zone will no longer be a zone without a no pump flag. To avoid a continuous loop, the step of determining whether all of the zones are in no pump mode 188 is performed. If all zones are not in the no pump mode then the select zone step 172 is performed. However if all zones are in the no pump mode, the pumping procedure 131 is exited and the venting procedure 133 is performed. During the exit from pumping procedure 131 to venting procedure 133 the steps of clearing each zone out of no pump mode by clearing the no pump flags 190 and turning off the pump 192 are performed.

Venting procedure 133 includes the steps of opening the vent valve 200, selecting the valve to the next zone which is not in a no vent mode 202, measuring the current pressure ($P_\#$) in the selected zone 204, comparing the current pressure ($P_\#$) in the selected zone to a predetermined min pressure for that zone ($P_{\#min}$) 206. If the current pressure is greater than the min pressure ($P_\# > P_{\#min}$) for the zone the step of reading the current force ($F_\#$) on the zone 208 is performed, however, if the current pressure is less than the minimum pressure then the step of putting the zone into no vent mode by setting the no vent flag for the zone 210 is performed as part of a loop described later either returning to the zone selection step 202 of venting procedure 133 or exiting to pumping procedure 131.

As long as the current pressure does not dip below the minimum pressure for the zone, the step of comparing the current force to the last recorded force on the zone 212 is performed. If the current force on the zone is less than the last recorded force, the goal of minimizing forces is being achieved by what is currently being performed, i.e., venting, so the steps of replacing the recorded force with the current force ($F_{\#old} = F_\#$) 214 and venting the zone for a set period of time 216 are performed during a loop that returns to the select zone step 202 of venting procedure 133.

If during the comparison step 212 it is determined that the current force is not lower than the previously recorded force ($F_\# \geq F_{\#old}$), then whatever is currently being performed, i.e., venting, is not achieving the desired results for the selected zone. Therefore the zone is not vented anymore and the step of setting a No Vent Flag ($NVF_\#$) to establish that the zone is in a "no-vent mode" 210 is performed as part of a possible venting procedure exit loop. Anytime the no vent mode step 210 is performed for a zone, that zone cannot be selected anymore during the current venting procedure as the zone will no longer be a zone without a no vent flag. To avoid a continuous loop, the step of determining whether all of the zones are in no vent mode 218 is performed. If all zones are not in the no vent mode then the select zone step 202 is performed. However, if all zones are in the no vent mode, then the venting procedure 133 is exited and the pumping procedure 131 is performed. During the exit from venting procedure 133 to pumping procedure 131 the steps of clearing each zone out of no vent mode by clearing the no vent flags 220 and closing the vent valve 222 are performed.

Figure 9:
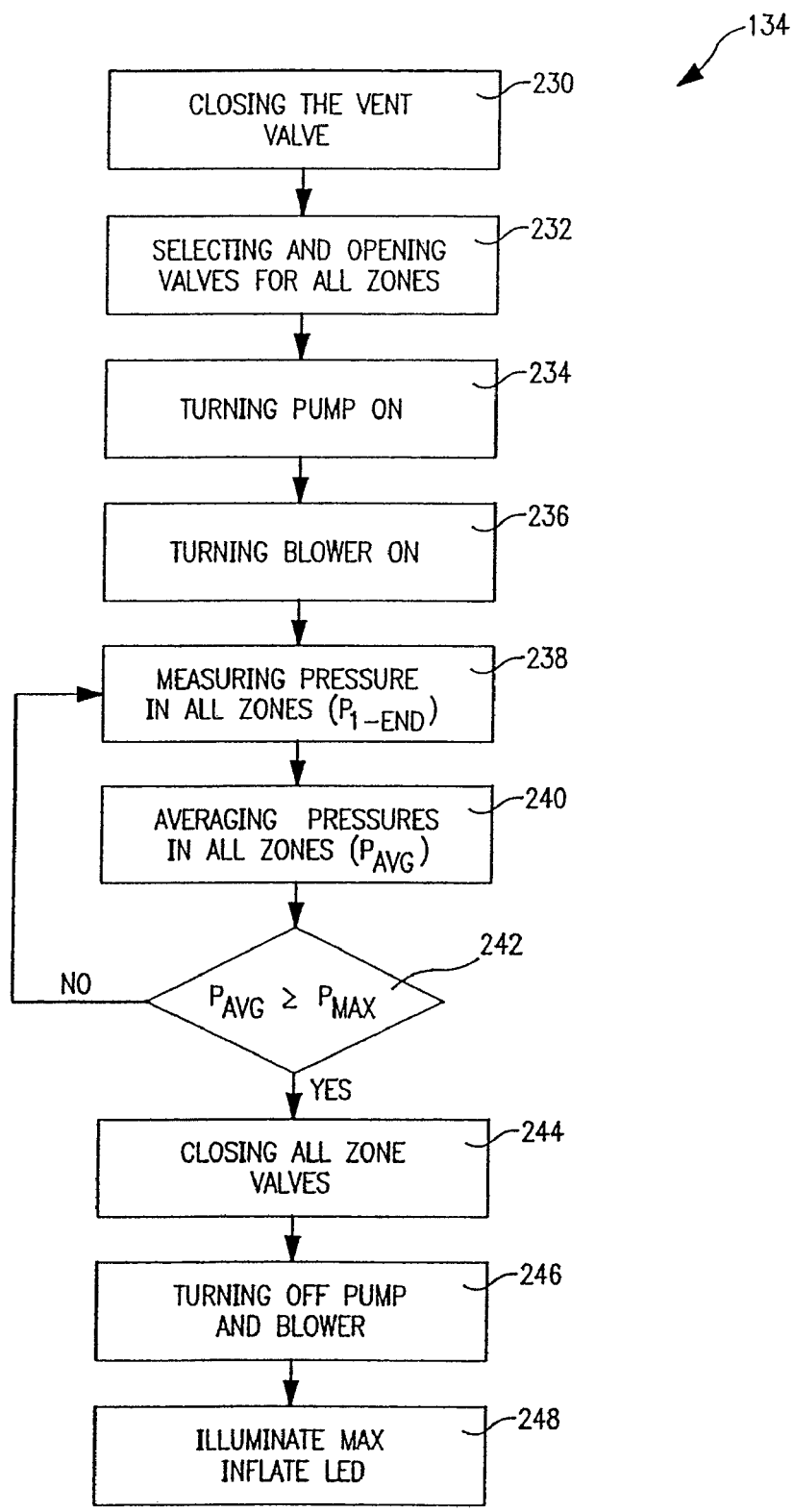
FIG. 9 is a flow diagram of the algorithm for a max inflate mode for controlling the inflation of the zones of the air support layer in accordance with the present disclosure.
Figure 10:
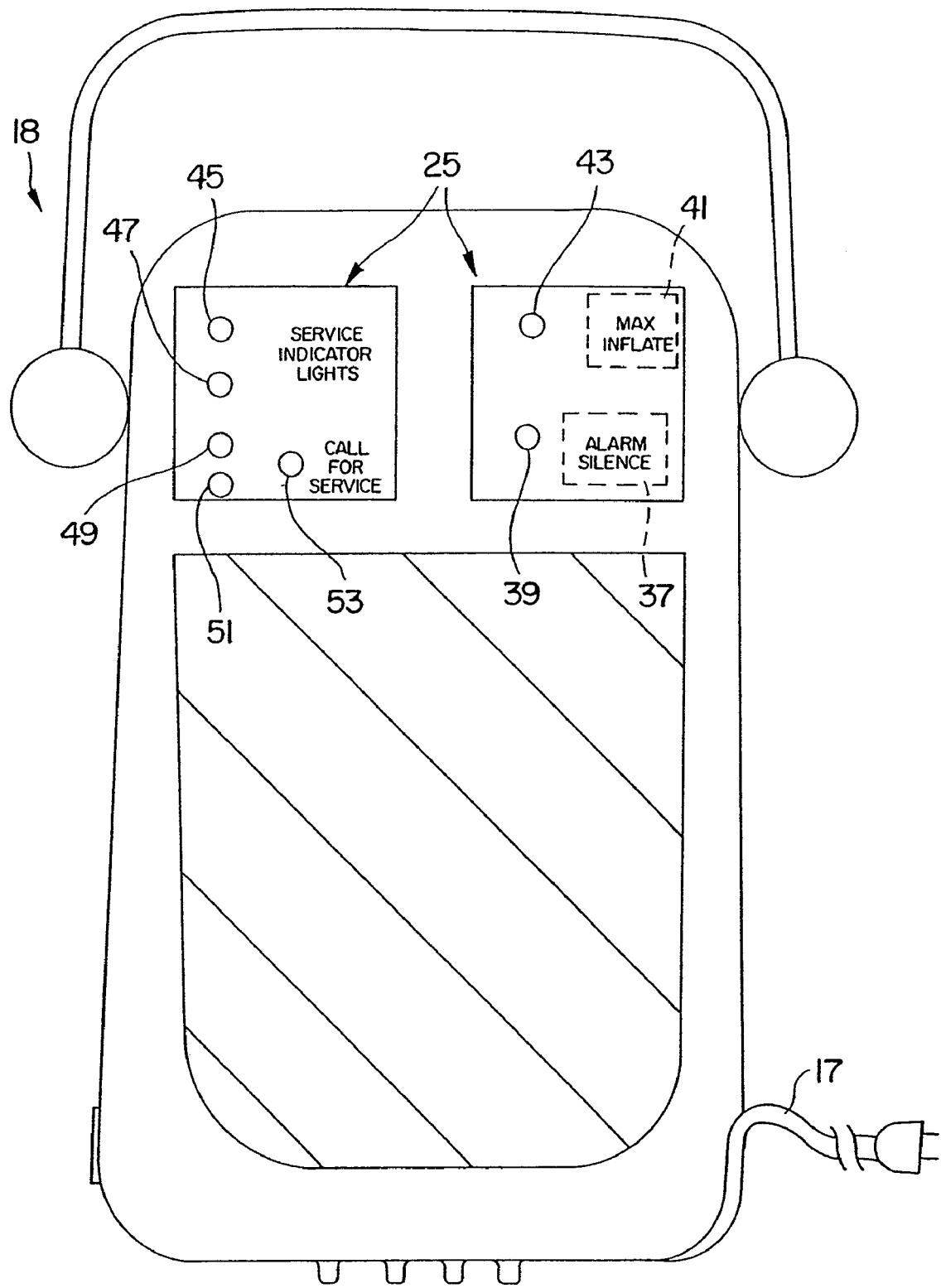
FIG. 10 is a front view of the controller of FIG. 1 showing various switches and indicators for monitoring and controlling force optimization surface.
Figure 11:
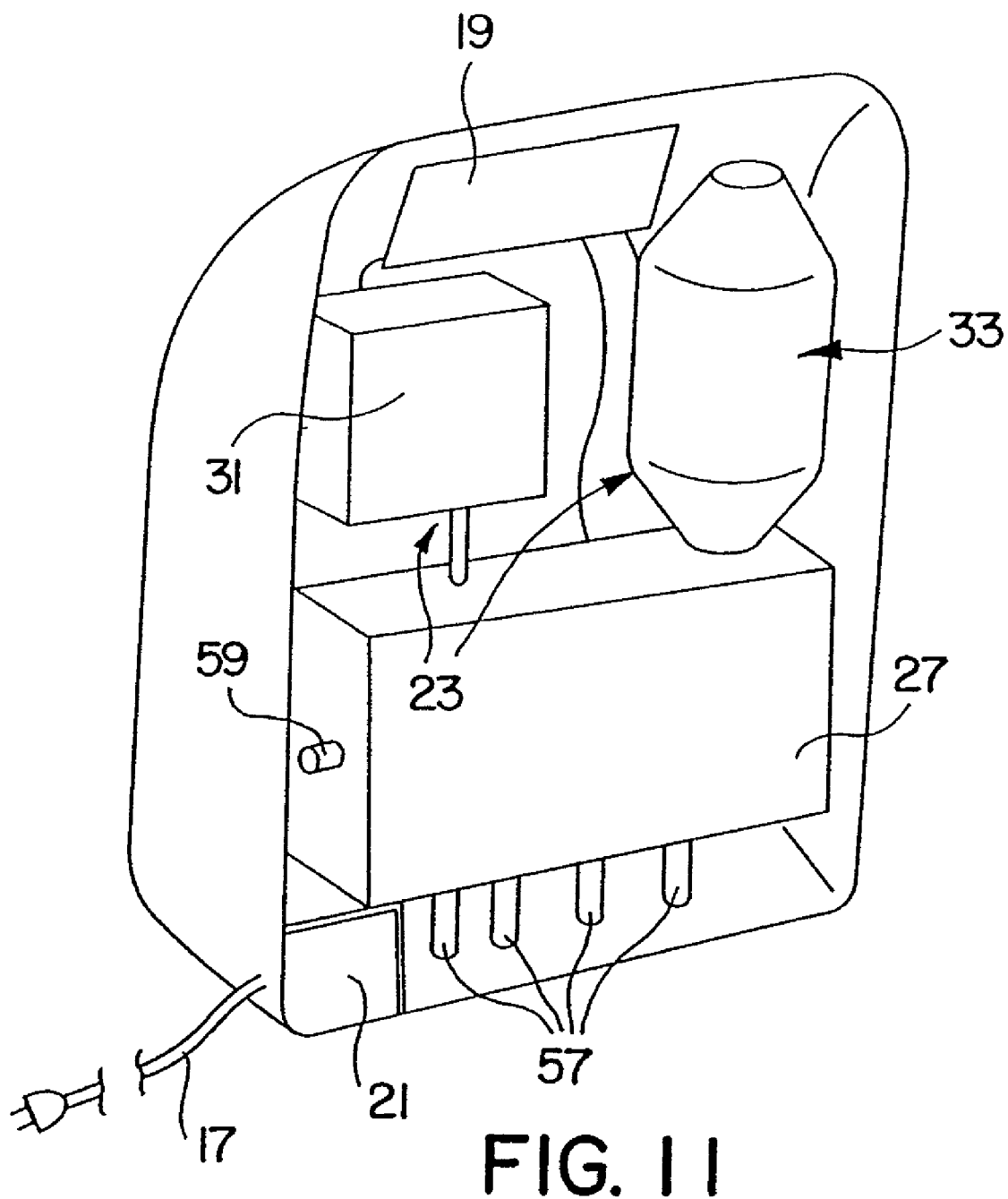
FIG. 11 is a back view of the controller with back panel removed to show the valve assembly, compressor, and blower used in controlling the pressure in zones of the force optimization surface.

The control algorithm also includes a max inflate mode 134, shown, for example, in FIG. 9. The max inflate mode 134 includes the steps of closing the vent valve 230, opening the valve for all of the zones 232, turning the pump on 234, turning the blower on 236, measuring the pressure in each zone 238, and averaging the pressures in all of the zones ($P_{avg}$) 240. Then the step of comparing the average pressure to the maximum pressure 242 is performed. If the average pressure is not less than the maximum pressure ($P_{avg\#} \geq P_{max}$), then the steps of closing all of the valves 244, turning off the pump and blower 246, and illuminating the max inflate LED 248 are performed. If the average pressure is less than the maximum pressure ($P_{avg} \leq P_{max}$) then max inflate mode returns to the measuring pressure step 238.

The control algorithm also includes a call for service mode. A maximum service time will be selected. If the maximum service time has elapsed, the return from any pressure transducer equals zero, or if pressure does not rise in any zone after max service time, or if force readings are open or short circuit for max service time, the call for service LED 53 is illuminated.

While the disclosure thus far has been described as including four chambers and four sensing zones positioned between the four chambers and a surface on which a patient is located with each zone being responsive to changes in interface pressure or force over an associated chamber, it is within the teaching of the disclosure to include more or less than four chambers and four zones. Those skilled in the art to which this disclosure relate will recognize that higher resolution and greater control can be achieved by increasing the number of independently inflatable chambers or modifiable zones and associated sensor zones. It should also be recognized that independently inflatable chambers or modifiable zones and associated sensor zones can assume any configuration, orientation, or arrangement to facilitate controlling interface forces between patient and a surface on which patient is situated. In other words, zones can extend along a separate the support surface along both a length dimension and a width dimension of the support surface.

Controller 18 is configured to monitor peak interface force on a zone between patient 16 and mattress 12 and can reduce that force by adjusting pressure in one or more chambers. Controller 18 includes memory for storing and recording data such as sensor values and adjustments made over time. The data recorded by controller 18 can be used to analyze system performance and make assessments regarding patient 16. Controller 18 is further configured to interface with a display and/or printer output device 22 to provide for either visual or hard copy output both for recorded data and for data as it is acquired in real time.

Force optimization surface 10 further can be configured with a weighing system to sense, monitor, record, display, and print patient 16's weight. When a large number of force sensors are used, by integrating measured force values, interface sensors 15 can be used to derive weight information. However in the illustrated embodiment separate weight sensors 24 (diagrammatically illustrated only) are provided, such as force sensors in a bottom layer (not shown) of surface 10. One such force sensor includes a single bladder (not shown) internally lined with conductive material to indicate bottoming out so that the pressure in the bladder will be proportional to the weight of the patient when bottoming out is not indicated. A separate reference chamber is provided to determine the weight differential. As with interface sensors 15, a grid of weight sensors 24 can capture patient weight without adverse effect from either the orientation of force optimization surface 10 atop an articulated frame or the orientation of patient 16 atop surface 10. Although weight sensors 24 can provide an absolute weight value, controller 18 can be configured to determine accurate weight change values from weight sensors 24 even if a precise absolute weight is not easily obtained. Even without an accurate absolute weight of patient 16, a caregiver can derive meaningful information concerning patient 16 based on knowledge of weight changes over time. Controller 18 can further be configured to detect a bed exit by patient 16 based on information from weight sensors 24, and provide an alert to caregivers accordingly.

An embodiment of force optimization surface 10 also includes integrated diagnostic sensors such as heart rate, respiration, and temperature sensors 26, 28, 30. Interface sensors 15 are used to obtain this information by monitoring pressure changes in real-time and analyzing the data to derive the vital characteristics. Software filters detect the appropriate respiration or heart rate signals. Non-invasive sensor systems for obtaining these patient parameters as are known in the art can also illustratively be integrated into force optimization surface 10 by embedding them into sensor layer 14. Temperature can be obtained through temperature sensing transducers or fabrics as are also known in the art. For example, thermistors may be provided in the piezo resistive sensing layer discussed above. These technologies provide diagnostic capabilities in that controller 18 can monitor and display vital signs of patient 16 such as heart rate, respiration rate, and skin temperature. Useful information about a patient 16 is provided both by display of the current values of these parameters and by analysis of this information recorded by controller 18 over a period of time.

Controller 18 includes software to monitor these conditions and provide alerts 32 when vital signs go out of predefined bounds. Various levels of alerts 32 can be provided, ranging from informational alerts for relatively minor deviations to emergency alerts upon detection of life threatening conditions. Controller 18 can be coupled to other systems to signal these alerts, such as a system at a nurse station, an automated paging system, etc.

Controller 18 uses information from sensors 15, 26, 28, 30 to derive other diagnostic information related to patient 16, such as an apnea condition based on monitoring of respiration rate based on interface pressure sensors 15 or from respiration sensor 28. Vital sign information from sensors 15, 26, 28, 30 can also be correlated to other measurements such as patient core temperature, pulse oximetry, etc. Force optimization surface 10 can further be configured with a vibrating mechanism that is activated by controller 18 upon detection of an apnea condition, in order to vibrate patient 16 gently to induce recovery. An alarm can be indicated if the apnea condition persists beyond a predetermined amount of time.

Force optimization surface 10 can further be configured to measure interface shear forces or pressures between patient 16 and surface 10 which can also restrict blood flow to patient 16 and contribute to development of pressure ulcers. Interface pressure sensors 15 as discussed above provide measuring a normal force. By providing sensors 15 that also sense shear forces, or separate shear force sensors (not shown), controller 18 can be configured to adjust air pressures in chambers of mattress 12 based on both normal and shear forces if the anti-shear layer 40 is not incorporated in support surface assembly 11.

Although certain illustrative embodiments have been described in detail above, variations and modifications exist within the scope and spirit of this disclosure as described and as defined in the following claims.

The invention claimed is:

1. A patient support surface comprising:
a cover defining an interior region,
a modifiable support layer situated in the interior region and having at least one air bladder, and
a sensor layer situated in the interior region above the at least one air bladder and having at least one sensor configured to detect a physiological parameter of a patient atop the patient support surface, the physiological parameter comprising at least one vital sign of the patient, the at least one sensor comprising a first sensor having a first output signal from which the at least one vital sign is determined, and the sensor layer comprising a second sensor having a second output signal which is used to determine whether to adjust a pressure of the at least one air bladder.

2. The patient support surface of claim 1, wherein the first sensor comprises one of a hear rate sensor, a respiration rate sensor, and a temperature sensor and the second sensor comprises a force sensor.

3. The patient support surface of claim 2, wherein the sensor layer comprises a piezoelectric material located between the modifiable support layer and the cover.

4. The patient support surface of claim 1, wherein the physiological parameter is one of a heart rate, a respiration rate, a body temperature, and blood oxygenation.

5. The patient support surface of claim 1, wherein the at least one sensor comprises a plurality of sensors configured to detect a plurality of physiological parameters of a patient atop the patient support surface.

6. The patient support surface of claim 5, wherein the plurality of physiological parameters comprise one or more of a heart rate, a respiration rate, a body temperature, and blood oxygenation.

7. The patient support surface of claim 1, further comprising a controller configured to generate an alert if a physiological parameter derived from the at least one sensor goes outside a predefined range.

8. The patient support surface of claim 7, wherein the controller is further configured to generate an alert at a nurse station and/or over an automated paging system if a physiological parameter derived from the at least one sensor goes outside a predefined range.

9. The patient support surface of claim 7, wherein the controller is configured to activate an alarm if the physiological parameter derived from the at least one sensor goes outside the predefined range.

10. The patient support surface of claim 1, further comprising a controller configured to monitor an apnea condition of a patient atop the patient support surface based on information from the at least one sensor.

11. A patient support surface comprising:
a cover defining an interior region,
a modifiable support layer situated in the interior region and having at least one air bladder,
a sensor layer situated in the interior region and having at least one sensor configured to detect a physiological parameter of a patient atop the patient support surface, and
a controller configured to monitor an apnea condition of a patient atop the patient support surface based on information from the at least one sensor,
wherein the controller is configured to vibrate the patient support surface upon detection of an apnea condition.

12. The patient support surface of claim 10, wherein the controller is configured to activate an alarm if the apnea condition persists beyond a predetermined amount of time.

13. The patient support surface of claim 1, wherein the sensor layer comprises a weight sensor.

14. The patient support surface of claim 13, wherein the weight sensor comprises a pressure sensing material.

15. The patient support surface of claim 13, further comprising a controller configured to monitor a patient's weight or changes in a patient's weight based on information received from the weight sensor.

16. The patient support surface of claim 1, wherein the modifiable support layer comprises a plurality of independently controllable pressure sections, the sensor layer comprises a plurality of sensing zones, and each sensing zone has at least one force sensor, wherein one of the plurality of sensing zones comprises the first sensor, and wherein one of the plurality of independently controllable pressure sections comprises the at least one air bladder.

17. The patient support surface of claim 16, further comprising a controller configured to adjust pressure in the independently controllable pressure sections based on an interface force for each section sensed by the associated at least one force sensor and the second output signal is indicative of one of the interface forces associated with the corresponding independently controllable pressure section.

18. The patient support surface of claim 17, wherein the controller is configured to adjust pressure in the independently controllable pressure sections to minimize the interface force for each section.

19. The patient support surface of claim 1, further comprising a fire barrier configured to enclose the modifiable support layer and the sensor layer.

20. The patient support surface of claim 1, further comprising an anti-sheer layer located between the cover and the sensor layer.

21. The patient support surface of claim 1, wherein the modifiable support layer includes a lower foam/air support layer and an upper controllable air mattress layer.

22. A support surface apparatus for supporting a person laying thereon, the support surface apparatus comprising:
a cover defining an interior region,
a modifiable support layer situated in the interior region and having at least one air bladder,
a sensor layer situated in the interior region above the at least one air bladder and having a first sensor and a second sensor, and
a controller coupled to the first and second sensors, the controller being configured to determine at least one vital sign of the person based on a first output signal from the first sensor and the controller configured to adjust pressure in the at least one air bladder based on a second output signal from the second sensor.

23. The apparatus of claim 22, wherein the second sensor comprises a force sensor, and the controller is configured to adjust pressure in the at least one air bladder based on an interface force sensed by the force sensor.

24. The apparatus of claim 22, wherein the at least one first sensor is configured to sense heart rate.

25. The apparatus of claim 24, wherein the controller includes a software filter.

26. The apparatus of claim 24, wherein the vital sign is one of pulse rate and respiration rate.

27. A patient support surface comprising:
a cover defining an interior region,
a modifiable support layer situated in the interior region and having at least one air bladder, and
a sensor layer situated in the interior region and having at least one temperature sensor to measure a temperature of a patient, the sensor layer further comprising a first sensor having a first output signal from which at least one vital sign of the patient is determined and a second sensor having a second output signal which is used to determine whether to adjust a pressure of the at least one air bladder.

28. The patient support surface of claim 27, further comprising a controller configured to monitor a patient's temperature or changes in a patient's temperature based on information received from the at least one temperature sensor.

29. The patient support surface of claim 27 wherein the at least one temperature sensor comprises a temperature sensing fabric.

30. The patient support surface of claim 27, wherein the at least one temperature sensor comprises at least one thermistor.

31. A method for monitoring a physiological parameter of a patient supported on a patient support surface, the method comprising:
providing a cover defining an interior region,
providing a modifiable support layer having at least one air bladder,
providing a sensor layer above the at least one air bladder and having at least one physiological parameter sensor configured to sense at least one vital sign of a patient, the sensor layer also having at least one force sensor,
enclosing the modifiable support layer and the sensor layer within the interior region of the cover to define the patient support surface, determining a vital sign of the patient based on a first output signal from the at least one physiological parameter sensor, and determining whether to adjust an air pressure in the at least one air bladder based on a second output signal from the force sensor.

32. The method of claim 31, wherein enclosing the modifiable support layer and the sensor layer within the interior region of the cover comprises joining a top cover portion with a bottom cover portion along a seam.

33. The method of claim 31, wherein the physiological parameter sensor is one of a heart rate sensor, a respiration rate sensor, a body temperature sensor, and blood oxygenation sensor.

34. The method of claim 31, further comprising providing a controller configured to detect a physiological parameter of a patient atop the patient support surface based on information received from the at least one sensor.

35. The method of claim 34, wherein the controller is further configured to generate an alert if a physiological parameter derived from the at least one physiological sensor goes outside a predefined range.

36. The method of claim 34, wherein the controller is further configured to generate an alert at a nurse station and/or over an automated paging system if a physiological parameter derived from the at least one physiological sensor goes outside a predefined range.

37. The method of claim 31, further comprising providing a controller configured to monitor an apnea condition of a patient atop the patient support surface based on information received from the at least one physiological sensor.

38. A method for monitoring a physiological parameter of a patient supported on a patient support surface, the method comprising:

providing a cover defining an interior region, providing a modifiable support layer having at least one air bladder, providing a sensor layer having at least one physiological parameter sensor, and enclosing the modifiable support layer and the sensor layer within the interior region of the cover to define the patient support surface, providing a controller configured to monitor an apnea condition of a patient atop the patient support surface based on information received from the at least one physiological sensor, and vibrating the patient support surface upon detection of an apnea condition.

39. The method of claim 37, further comprising generating an alarm if the apnea condition persists beyond a predetermined amount of time.

40. The method of claim 31, further comprising a controller configured to determine a patient's weight or changes in a patient's weight based on information received from at least one weight sensor.

* * * * *